US006627411B2

(12) United States Patent
Maekawa et al.

(10) Patent No.: US 6,627,411 B2
(45) Date of Patent: Sep. 30, 2003

(54) METHOD FOR EVALUATING MATRIX METALLOPROTEASE INHIBITORY ACTIVITY

(75) Inventors: Ryuji Maekawa, Osaka (JP); Takayuki Yoshioka, Osaka (JP); Rhoichi Nemori, Minamiashigara (JP); Yutaka Tamura, Minamiashigara (JP)

(73) Assignees: Shionogi & Co., Ltd., Osaka (JP); Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/979,510

(22) PCT Filed: May 23, 2000

(86) PCT No.: PCT/JP00/03270

§ 371 (c)(1),
(2), (4) Date: Nov. 23, 2001

(87) PCT Pub. No.: WO00/71167

PCT Pub. Date: Nov. 30, 2000

(65) Prior Publication Data

US 2003/0157585 A1 Aug. 21, 2003

(30) Foreign Application Priority Data

May 24, 1999 (JP) ............................................. 11-143308
Jul. 27, 1999 (JP) ............................................. 11-212145

(51) Int. Cl.[7] ............................. C12Q 1/37; C12Q 1/02; C12Q 1/00

(52) U.S. Cl. ................................ 435/23; 435/29; 435/4
(58) Field of Search ................................. 435/23, 29, 4

(56) References Cited

U.S. PATENT DOCUMENTS 5,482,848 A  *  1/1996  Dickson et al. ............. 435/219
5,866,570 A  *  2/1999  Liang et al. ............. 514/232.2

FOREIGN PATENT DOCUMENTS

EP  0 884 393  12/1998
JP  10-45632  2/1998
JP  11-127896  5/1999

OTHER PUBLICATIONS

Hiroyuki Nakamura et al., "Enhanced Production and Activation of Progelatinase A Medicated by Membrane Type 1 Matrix Metalloproteinase in Human Papillary Thyroid Carcinomas", *Cancer Research*, Jan. 15, 1999, vol. 59, No. 2, pp. 467–473.

* cited by examiner

*Primary Examiner*—Louise N. Leary
(74) *Attorney, Agent, or Firm*—Wenderoth, Lind & Ponack, L.L.P.

(57) ABSTRACT

A method for checking a matrix metalloproteinase-inhibitory activity present in a mammal that has received a compound exhibiting matrix metalloproteinase-inhibitory activity, which comprises utilizing in situ zymography, is provided.

19 Claims, 2 Drawing Sheets

*In situ* film zymography (lower) and H.E. stain (upper) of Ma44 tumor tissues** Bar = 380 μm
(A) vehicle only, (B) [-]BPHA 200mg/Kg P.O., (C) BPHA 200mg/Kg P.O.

METHOD FOR EVALUATING MATRIX METALLOPROTEASE INHIBITORY ACTIVITY

This application is a 371 application of PCT/JP00/03270 filed May 23, 2000.

TECHNICAL FIELD

The present invention relates to a method for evaluating a compound exhibiting matrix metalloproteinase-inhibitory activity for an in vivo matrix metalloproteinase-inhibitory activity displayed by the compound, and specifically to a method therefor which comprises utilizing in situ zymography.

BACKGROUND ART

Matrix metalloproteinase (MMP) is a common name of enzymes which are secreted by cancer cells or normal cells surrounding cancers, and degrade extracellular matrix proteins such as collagen in a divalent metal ions-dependent manner. In particular, it has been frequently reported that type IV collagenases (MMP-2, MMP-9) are responsible for vascularization accompanied by tumor proliferation, and for tumor invasion and metastasis.

As an assay system for measuring matrix metalloproteinase, a gelatin zymography method is known wherein enzyme activities are determined based on degradation degree of a substrate. The method requires conducting electrophoresis, and therefore it is troublesome in the procedures, and time-consuming in the detection.

As an assay system without electrophoresis, *The FASEB Journal*, vol.9, July, pp.974–980, 1995 has proposed a determination method based on the principle of zymography, which comprises incorporating, into agarose, casein or gelatin bound to a fluorescent compound useful as a substrate for the protease, forming the mixture into a thin membrane on slide glass, then placing a tissue section on the surface of a thin membrane, incubating the membrane, and observing the digestion of the substrate by a fluorescence microscopy. The system, however, encounters a trouble with decreased reproducibility, since the agarose affects the digestion of the substrate due to the protease.

Recently, the applicants of the present application proposed a convenient and accurate method for measuring proteases, which comprises contacting a sample containing a protease to a thin membrane formed on the surface of a support, said thin membrane comprising a protease substrate and a hardening agent (WO97/32035), which have received some signs of confidence. For example, Proceedings of 5th Conference of the Japanese Association for Metastasis Research (1996) describes that in situ zymography based on our method was used to detect the gelatinase activity in the tissue and cells, thus observing that the protease destroyed tumor tissues. In situ zymography is described in *The FEBS Journal*, 974–980, Vol. 9 (1995) or the like.

Further, H. Nakamura, et al. *Cancer Research* 59,467–473(1999) describes that in situ zymography similarly revealed that MMP inhibitors inhibited the MMP activity in human thyroid cancer.

As described above, MMPs, in particular type IV collagenase, are believed to be responsible for vascularization accompanied by tumor proliferation, and for tumor invasion and metastasis. Accordingly, inhibitors of MMPs have been a focus of attention in view of development of anti-cancer agents, and, in fact, some of them are clinically being tested by some pharmaceutical companies.

Pharmacotherapy is achieved on the prerequisite that a drug used in the therapy is effective and safe, and the prerequisite is confirmed by drug evaluation, which is largely classified into two tests, nonclinical test such as animal experimentation, and clinical test wherein human beings are tested. Even agents that are effective in the nonclinical test, or have an excellent action mechanism would not be drugs when the agents are not effective in patients. This is the reason why the clinical test is required to evaluate the drug efficacy in humans.

In drug evaluation of MMP inhibitors by the clinical test, it is difficult to determine exactly the in vivo activity of MMP inhibitors because MMP is inherently controlled in vivo by endogenous inhibitors such as TIMP-1, and -2 [Woessner, J. F. Jr., *FASEB J.* 5, 2145–54 (1991)]. Immunostaining method wherein an antibody specific to MMP is used has been known as a method for detecting MMP (*Int. J. Cancer.*, 56, 500–505 (1994)). Since the antibody used therein, however, recognizes MMP in a manner that MMP is merely an antigen protein, this method dose not allow to determine whether an antigen protein recognized by the antibody possesses the MMP activity or is inactivated by the inhibitors. Conventional gelatin zymography dissociates MMP from inhibitors during the electrophoresis, and therefore the method does not also allow the exact determination of the inhibitory activity of MMP inhibitors.

PROBLEMS TO BE SOLVED

In view of the above, the present inventors investigated for a method of checking the in vivo activity of MMP inhibitors, and found that in situ zmography makes it possible to determine conveniently and rapidly the in vivo MMP inhibitory activity of MMP inhibitors.

MEANS TO SOLVE THE PROBLEMS

In the first aspect, the present invention relates to a method for evaluating a compound exhibiting matrix metalloproteinase-inhibitory activity for an in vivo matrix metalloproteinase-inhibitory activity displayed by the compound, which comprises subjecting to in situ zymography a specimen isolated from a mammal that has received the compound.

Specifically, the present invention relates to the method wherein the in situ zymography is conducted using a thin membrane which comprises gelatin or collagen together with a hardening agent, and which has a thickness of 1 µm to 20 µm. More specifically, the in situ zymography is conducted by (1) contacting the isolated specimen onto the thin membrane comprising a substrate of matrix metalloproteinase;

(2) incubating the specimen-thin membrane sample;

(3) staining and then decolorizing the thin membrane; and (4) verifying the tone developed on the thin membrane.

In the evaluation method of the present invention, it is preferred that the substrate of matrix metalloproteinase is gelatin or collagen; that the thin membrane comprises a hardening agent; that the thin membrane has a thickness of 1 µm to 20 µm; and/or that the specimen is a tissue section, preferably a lyophilized tissue section, having a thickness of 2 µm to 10 µm, and the incubation is conducted at 20° C. to 50° C., preferably 36 to 38° C., for 2 to 18 hours.

In the second aspect, the present invention relates to a method for evaluating a compound exhibiting matrix metalloproteinase-inhibitory activity for an in vivo matrix metalloproteinase-inhibitory activity displayed by the compound, which comprises:

(1) administering to a mammal a compound exhibiting matrix metalloproteinase-inhibitory activity; (2) isolating a tissue or a fluid from the mammal to prepare a specimen; (3) contacting the isolated specimen onto a thin membrane comprising a substrate of matrix metalloproteinase; (4) incubating the specimen-thin membrane sample; (5) staining and then decolorizing the thin membrane; and (6) verifying the tone developed on the thin membrane.

In the third aspect, the present invention relates to a method for evaluating an anti-cancer agent exhibiting matrix metalloproteinase-inhibitory activity for its anti-cancer activity, which comprises subjecting to in situ zymography a specimen isolated from a mammal that has received the anti-cancer agent, and evaluating for an in vivo matrix metalloproteinase-inhibitory activity displayed by the agent as an indicator of the anti-cancer activity. In the method of the present invention, it is preferred that the substrate of matrix metalloproteinase is gelatin or collagen; that the thin membrane comprises a hardening agent; that the thin membrane has a thickness of 1 $\mu$m to 20 $\mu$m; and/or that the specimen is a tissue section, preferably a lyophilized tissue section, having a thickness of 2 $\mu$m to 10 $\mu$m, and the incubation is conducted at 20° C. to 50° C., preferably 36 to 38° C., for 2 to 18 hours.

It has been known that not only MMP but also many enzymes that degrade gelatin, such as trypsin, exist in the living body. For this reason, it was difficult to determine selectively the activity of MMP inhibitors by manes of in situ zymography using substrates of MMP such as gelatin, as used in the present invention. No method for determining an in vivo matrix metalloproteinase-inhibitory activity of MMP inhibitors has been known.

As used herein, "in situ zymography" means an in vitro method useful for determination of protease activities, which is not involved in electrophoresis. In the present invention, this is conducted by contacting onto a thin membrane comprising a substrate of matrix metalloproteinase an specimen isolated from a mammal receiving a compound exhibiting matrix metalloproteinase-inhibitory activity (MMP inhibitor), and observing the MMP substrate after the lapse of a defined period of time, so that the inhibitor is evaluated for "in vivo MMP inhibitory activity".

The term "mammal" in the phrase "specimen isolated from a mammal" means a higher vertebrate, preferably human being, which has been administered with a MMP inhibitor. The test object in this method is a specimen isolated from the living body, which provides a result exactly corresponding to an in vivo MMP inhibitory activity of a MMP inhibitor, which the inhibitor exerts in vivo.

"Specimen isolated" may be derived from various tissues and fluids, and is varied depending on efficacy or indication of MMP inhibitors to be administered into a mammal. When, for example, a MMP inhibitor is for an anti-cancer agent, a specimen is derived from cancerous tissue samples isolated and taken by surgical operation or histological examination from cancerous tissues such as breast cancer, endometrioma, cancer of buccal cavity, lung cancer, gastric cancer, esophageal cancer, epithelial cancer of urinary tract, colon cancer, squamous cancer, thyroid cancer. For an anti-rheumatic agent, synovial membranes or fluids, or bone tissues derived from patients with rheumatoid arthritis or arthritis are used, whereas for an agent for treating heart failure, heart tissues or effusions therefrom derived from patients with heart failure would be used. In this manner, the present invention may be utilized as methods for evaluating anti-cancer agents, anti-rheumatic agents, and agents for treating heart failure.

MODES FOR CARRYING OUT THE INVENTION

Figure 1:
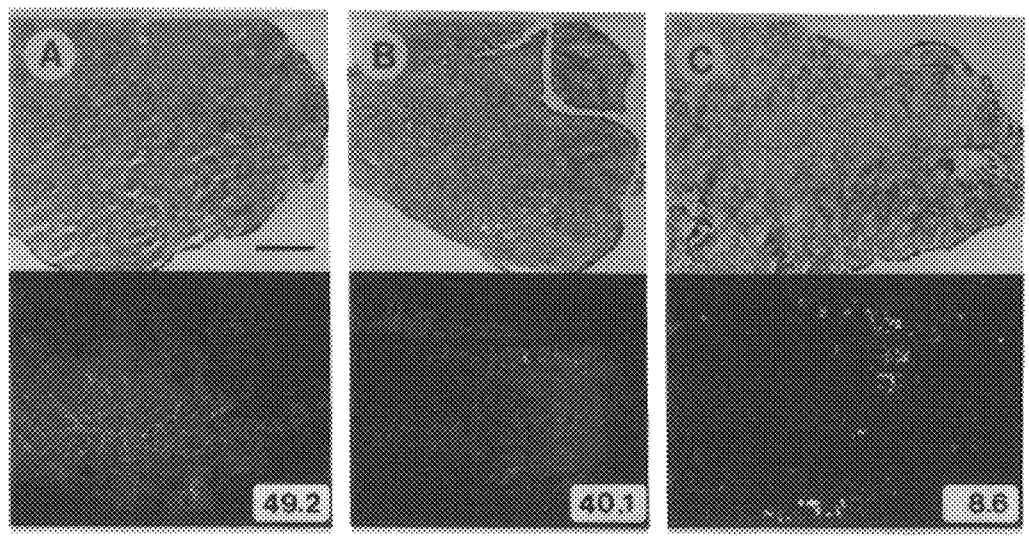
FIG. 1 is a picture substitute for drawings which shows the micrographs under light microscopy (the upper) of the carcinoma stained with H.E. in the mouse receiving an vehicle (A), the mouse receiving (–)BPHA (B), and the mouse receiving BPHA (C), as well as the in situ zymography therein regarding gelatin degradation (the lower).

"In situ zymography" in the present invention specifically comprises the steps of:

(1) contacting the isolated specimen onto the thin membrane comprising a substrate of matrix metalloproteinase;

(2) incubating the specimen-thin membrane sample;

(3) staining and then decolorizing the thin membrane; and (4) verifying the tone developed on the thin membrane.

Each of the steps is further described below.

(1) Contacting the isolated specimen onto the thin membrane comprising a substrate of matrix metalloproteinase "Contacting the specimen onto the file" means that the tissue removed is placed or attached onto the thin membrane, or the fluid taken is dropped onto the thin membrane.

"Isolated specimen" includes frozen sections having a thickness of 2 $\mu$m to 10 $\mu$m, preferably 4 $\mu$m to 8 $\mu$m, which are prepared from samples of tissues quickly frozen by use of for example liquid nitrogen with an apparatus for preparing frozen sections. Alternatively, body fluids such as blood, saliva, synovial fluid, and the like may be used. In case of the use of synovial fluid taken from patients with rheumatoid arthritis as a specimen, about 5 to 50 $\mu$l, preferably about 20 $\mu$l, of synovial fluid is dropped onto the thin membrane.

"MMP Substrate" is a macromolecular compound that is degradable by MMP, and includes for example gelatin, collagen, proteoglycan, fibronectin, laminin, elastin, and casein. Preferred one is gelatin, collagen, fibronectin, elastin or casein, and more preferred one is gelatin or collagen. MMP is described for example in Takashi Tsuruo ed., "*Molecular Mechanism for cancer metastasis*" pp.92–107 (1993) Medical View Publisher, and include, but is not limited to, proteases such as interstitial collagenase (MMP-1), gelatinase A (MMP-2), and gelatinase B (MMP-9).

"Thin membrane comprising a MMP substrate" means those prepared from a monolayer or a multilayer of the MMP substrate as described above which is formed on the surface of a support. The details are described in WO97/32035. In brief, the thin membrane is a monolayer or a multilayer having a thickness of 6 $\mu$m to 20 $\mu$m, particularly 8 $\mu$m to 10 $\mu$m, which layer is on a support, and the thin membrane preferably has the homogeneous surface.

The thin membrane as used in the method of the present invention preferably comprises a hardening agent. Hardening agent promotes the hardening of the thin membrane of MMP substrate, and/or prevents the formed thin membrane from swelling. The details of the hardening agent are described in WO97/32035. Hardening agents include vinyl sulfonyl type of hardening agents. In case of gelatin for example, it is advantageous to blend 0.1 to 20 mmol, preferably about 0.3 to 10 mmol, of a hardening agent to 100 g of gelatin in view of the detection capacity although amount of hardening agents is not particularly limited.

In addition to the agents as shown above, other components such as dyes, pigments, preservatives, stabilizers or the like can be comprised as appropriate to prepare the thin membranes.

"Support" is preferably transparent or semitransparent so as to allow the observation of the presence of MMP in tissues under a microscopy. Those transparent or semitransparent supports include a glass, and a transparent or semi-transparent plastic film composed of polyethylene terephthalate or the like. Although the thickness of the support is not particularly limited, a glass support having a thickness similar to slide glass (for example about 2 to 3 mm) is preferred, whereas a polyethylene terephthalate support having a thickness of about 100 to 250 $\mu$m may be used.

In order to prepare "thin membrane and support", a MMP substrate dispersed in water or an organic solvent such as acetone, methanol, ethanol or a mixture thereof for example is spread on the surface of a support, and then dried. As procedures for the spreading, dip coating method, roller coating method, curtain coating method, extrusion coating method, and the like, all of which are known in the art can be used. In case that gelatin is used as a MMP substrate, gelatin is not limited to any particular species, and for example an alkali-treated bovine bone gelatin, an acid-treated swine cutis gelatin, or the like may be used.

(2) Incubating the resulting specimen-thin membrane sample;

"Specimen-thin membrane sample" is one obtained after attaching the tissue section onto the thin membrane, or dropping the liquid specimen onto the thin membrane, so as to contact a MMP-containing specimen to the thin membrane.

"Incubating" means that a sample is left stand at 20° C. to 50° C., preferably 36° C. to 38° C. in a thermostat bath, and the incubation is preferably conducted in a humid bath in order to prevent the thin membrane from dryness. For example, tissue sections are incubated at 37° C. for 1 to 24 hours, preferably 2 to 18 hours, more preferably about 4 to 8 hours, whereas liquid samples are incubated for 0.5 to 12 hours, preferably 1 to 6 hours.

When a specimen contains any MMP that is even inactivated by MMP inhibitors, the protease degrades the MMP substrate in the thin membrane to form the trace of digestion thereon.

(3) Staining and then decolorizing the thin membrane;

The specimen-thin membrane sample obtained in step (2) is stained preferably with a stain solution. Stain solutions are those that stain the enzyme substrate, and include Amido Black, Coomassie Blue, Ponceau (Wako Pure Chemical Industries), Biebrich Scarlet (Aldrich). It is preferred to use a 0.5 to 2% solution of Amido Black.

Subsequently, the thin membrane stained is decolorized with an appropriate decolorizing agent, for example, a 70% methanol-10% acetic acid solution, and water.

(4) Verifying the tone developed on the thin membrane;

The thin membrane treated by the steps as shown above will develop stain tones of dark and light colorings (gradient) depending on the range of MMP substrate degradation, since an area where the MMP substrate is degraded should not be stained. Such tone is verified by the observation with naked eye or under a microscope, or by quantitative analysis using a slide scanner, a laser microscope, or the like. The fact that the area is stained shows that MMP is therein being inactivated by an action of a MMP inhibitor administered, or for other reasons. Determination whether the inactivation is caused by the MMP inhibitory action or by other reasons may be readily conducted by comparing it with a control wherein no MMP inhibitor is administered.

The present invention is directed to a method for evaluating a MMP inhibitor for an in vivo MMP-inhibitory activity displayed by the compound, and encompasses a method of the present invention which comprises as the first step administering a MMP inhibitor to a mammal. This makes it possible to evaluate an in vivo activity of a MMP inhibitor at the time when the inhibitor is administered to a patient during clinical test. The next steps are usually conducted setting a time interval of 30 minutes to four hours after the administration of a MMP inhibitor.

The present invention further encompasses a method for evaluating an anti-cancer agent exhibiting matrix metalloproteinase-inhibitory activity for its anti-cancer activity, which comprises subjecting to in situ zymography a specimen isolated from a mammal that has received the anti-cancer agent, and evaluating for an in vivo matrix metalloproteinase-inhibitory activity displayed by the agent as an indicator of the anti-cancer activity. Drug evaluation for anti-cancer agents in the clinical test has been conducted mainly based on a patient's life-extending effectiveness or subjective symptoms of patients, the presence or absence of tumor regression/metastasis, amounts of tumor markers, or the like. However, it is difficult that these indexes show whether the transition of drugs to the lesion is good or bad, and also provide fine selection of the dosage of drugs. On the other hand, the evaluation method for anti-cancer activity of the present invention, in the clinical test, enables to determine the dosage of agents or the schedule for administration, determine if the agent reaches cancer tissue, and provides a useful means to select types of cancers to be treated.

Such method of this aspect of the present invention is also conducted by each of the steps as described above.

According to the methods of the present invention, it can be checked if a cancer to be tested is dependent on MMP, thus providing a more appropriate method for the treatment for cancers.

The present invention is further illustrated by the following examples, but is not restricted by these examples in any way.

EXAMPLES

Example 1

Evaluation of MMP Inhibitors for Their Activity by in situ Zymography

MMP Inhibitors

In this test, compound BPHA of formula (I) exhibiting the MMP inhibitory activity, and compound (–)BPHA of formula (II) exhibiting no MMP inhibitory activity were used as test compounds for MMP inhibitors.

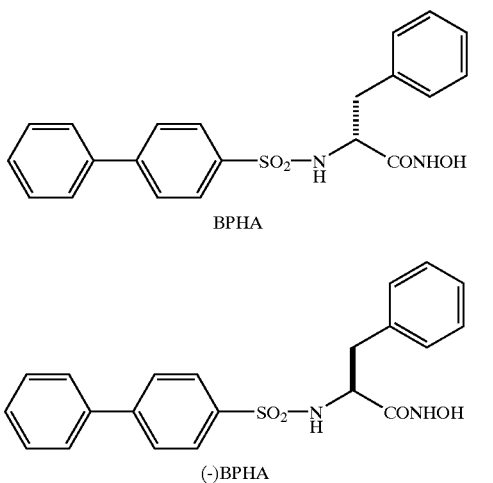

BPHA (I)

(-)BPHA (II)

TABLE 1

| Enzymes | IC50 (nM) | |
| --- | --- | --- |
| | BPHA | (-) BPHA |
| MMP-1 | 974 | >1000 |
| MMP-2 | 12 | >1000 |
| MMP-3 | >1000 | >1000 |
| MMP-7 | 795 | >1000 |
| MMP-9 | 16 | >1000 |
| MMP-14 | 17 | >1000 |

Preparation of gelatin thin membrane for the determination of protease activity

Fifteen g of acid-treated swine cutis gelatin was dissolved in 123 g of pure water, and the solution was added with 1.2 ml of 1,2-bis(vinylsulfonylacetamido)ethane (4%) as a hardening agent. The solution was uniformly applied to a polyethylene terephthalate film undercoated with gelatin so as to obtain a dried membrane having a thickness of about 7 µm, and the membrane was dried to obtain a gelatin thin membrane. The gelatin thin membrane was stored at room temperature until the use.

Cancer and Animal

Human lung cancer cell line Ma44 (*CANCER RESEARCH* 59, 1231–35 (1999)) that was known to produce MMP-2 in a large amount was used. Nude mice (six weeks aged, female, CLEA Japan, Inc.) were transplanted intraperitoneally with $1 \times 10^5$ Ma44 cells, and, 14 days later, BPHA or (-)BPHA was administered orally to the animals at 200 mg/kg. As control, a vehicle (a physiological saline containing 0.4% Tween80, 0.5% carboxymethyl cellulose, and 0.9% benzyl alcohol) was similarly administered. Two hours after the administration, the cancer-bearing mice were autopsied to remove the tumor mass formed at the abdominal wall and the mesenterium, and the mass was subjected to the in situ zymography experiment.

In situ Zymography

The tumor mass was embedded in OCT Compound (SAKURA), and then Microtone/Cryostat TISSUE TEK II (Miles-Sankyo) was used to prepare lyophilized sections having a thickness of 8 µm. The lyophilized sections were placed gently onto the gelatin thin membrane previously prepared to give samples, and then the membranes were placed into a humid bath to prevent them from drying, followed by leaving the membranes to stand in an incubator at 37° C. After reacted for 3.5 hours, the thin membranes were taken out, and stained with a 1% Amido Black solution (Wako Pure Chemical Industries) for 15 minutes. Subsequently, the membranes were treated with a decolorizing solution (70% methanol, 10% acetic acid) for 10 minutes.

The cancer tissue on the thin membrane was observed under light microscopy to determine the area where the gelatin degradation was recognized. Additionally, the slide scanner (Nikon 35 mm film scanner: COOLSCAN II) was used to analyze quantitatively the tone with the software Optimas Ver.6 (Optimas Corporation).

The micrographs under light microscopy of the cancer tissues stained with H.E. (hematoxylin and eosin) in the mouse receiving an vehicle, the mouse receiving (-)BPHA, and the mouse receiving BPHA, are shown at (A), (B), and (C) on the upper lane in FIG. 1, respectively. The results show that the tissues observed contain the cancer cells.

Additionally, the results obtained in the observation by the slide scanner are also shown at (A), (B), and (C) on the lower lane in FIG. 1. These show that the gelatin degradation was observed in the mouse receiving an vehicle and the mouse receiving (-)BPHA (the compound without MMP inhibitory activity), whereas little gelatin degradation was observed in the mouse receiving BPHA. Quantitative analysis using the software Optimas Ver.6 (brightness in each tissue/size in each tissue) was estimated at 49.2, 40.1, and 8.6 in the mouse receiving an vehicle, the mouse receiving (-)BPHA, and the mouse receiving BPHA, respectively.

The results are not inconsistent with those describing that BPHA exhibits the anti-cancer activity, whereas (-)BPHA does not in an animal experimentation (*CANCER RESEARCH* 59, 1231–35 (1999)).

Example 2

Observation of dose-dependent activity of MMP inhibitor using in situ zymography According to a similar manner to that of Example 1 except that MMI-166 of the formula:

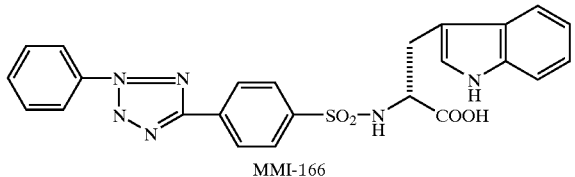

MMI-166 was orally administered at dosages of 0.2, 2.0, 20.0, and 200.0 mg/kg in stead of the administrations of BPHA and (-)BPHA, treatments were conducted for in situ zymography.

Figure 2:
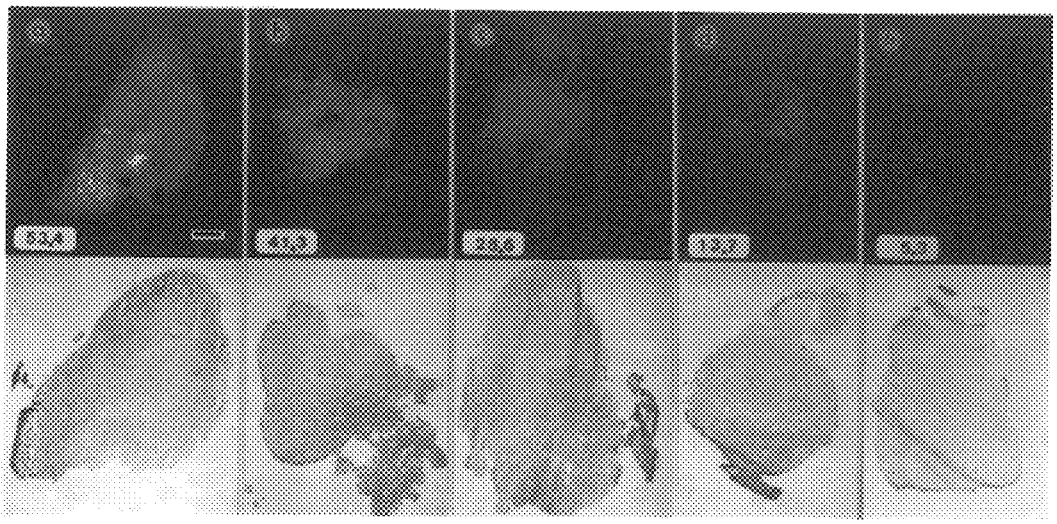
FIG. 2 is a picture substitute for drawings which shows the micrographs under light microscopy (the lower) of the carcinoma stained with H.E. in the mouse receiving an vehicle (a), and the mice receiving MMI-166 (b-e), as well as the in situ zymography therein regarding gelatin degradation (the upper).

The micrograph under light microscopy and the analysis of the slide scanner regarding gelatin degradation of the cancer tissues in the mouse receiving an vehicle and the mice receiving MMI-166 are shown at the lower lane and the upper lane in FIG. 2, respectively. In FIG. 2, (a), (b), (c), (d) and (e) are each results of the vehicle-receiving mouse, the 0.2 mg/kg-receiving mouse, the 2.0 mg/kg-receiveing mouse, 20.0 mg/kg-receiving mouse, and 200.0 mg/kg-receiving mouse. In the cancer tissue of the vehicle-receiving mouse, the gelatin degradation was recognized coincidentally at the cancer area (FIG. 2a). On the other hand, the results in the MMI-166-receiving mice were that the complete inhibition of the gelatin degradation was provided at the highest dosage 200.0 mg/kg, that the inhibition was lowered in sequence of 20.0 to 2.0 mg/kg, and that the merely partial inhibition was recognized at the dosage of 0.2 mg/kg (FIGS. 2e–b). According to these results, it was found that the inhibition of the gelatin-degrading activity observed at the cancer tissue was dependent on the MMI-166 dosage. Quantitative analysis using the software Optimas Ver.6 was also estimated at 53.4, 41.3, 28.6, 13.7, and 5.3, respectively.

The results as shown above suggest that the method of the present invention is useful to determine the dosage or the schedule for administration of compounds exhibiting MMP inhibitory activity required to inhibit actually gelatin degradation activity recognized at the cancer area.

EFFECTS OF THE INVENTION

The present invention makes in vitro determination of an in vivo activity of MMP inhibitors possible. The invention is useful to conduct drug evaluation in clinical test for anti-cancer agents, anti-rheumatic agents, and agents for treating heart failure, as well as elucidation of their action mechanism, specifically to determine the dosage or the administration schedule for the agents.

What is claimed is:

1. A method for evaluating a compound exhibiting matrix metalloprotease-inhibitory activity for an in vivo matrix metalloprotease-inhibitory activity displayed by the compound, which comprises subjecting to in situ zymography a specimen isolated from a mammal that has received the compound.

2. The method of claim 1, wherein the in situ zymography is conducted using a thin membrane which comprises gelatin or collagen together with a hardening agent, and which has a thickness of 1 $\mu$m to 20 $\mu$m.

3. The method of claim 1, wherein the in situ zymography is conducted by
   (1) contacting the isolated specimen onto the thin membrane comprising a substrate of matrix metalloprotease;
   (2) incubating the specimen-thin membrane sample;
   (3) staining and then decolorizing the thin membrane; and
   (4) verifying the tone developed on the thin membrane.

4. The method of claim 3, wherein the substrate of matrix metalloprotease is gelatin or collagen.

5. The method of claim 3, wherein the thin membrane comprises a hardening agent.

6. The method of claim 3, wherein the thin membrane has a thickness of 1 $\mu$m to 20 $\mu$m.

7. The method of claim 3, wherein the specimen is a tissue section having a thickness of 2 $\mu$m to 10 $\mu$m, and the incubation is conducted at 20° C. to 50 ° C. for 2 to 18 hours.

8. A method for evaluating a compound exhibiting matrix metalloprotease-inhibitory activity for an in vivo matrix metalloprotease-inhibitory activity displayed by the compound, which comprises:
   (1) administering to a mammal a compound exhibiting matrix metalloprotease-inhibitory activity;
   (2) isolating a tissue or a fluid from the mammal to prepare a specimen;
   (3) contacting the isolated specimen onto a thin membrane comprising a substrate of matrix metalloprotease;
   (4) incubating the specimen-thin membrane sample;
   (5) staining and then decolorizing the thin membrane; and
   (6) verifying the tone developed on the thin membrane.

9. A method for evaluating an anti-cancer agent exhibiting matrix metalloprotease-inhibitory activity for its anti-cancer activity, which comprises subjecting to in situ zymography a specimen isolated from a mammal that has received the anti-cancer agent, and evaluating for an in vivo matrix metalloprotease-inhibitory activity displayed by the agent as an indicator of the anti-cancer activity.

10. A method for determining quantitatively an in vivo matrix metalloprotease-inhibitory activity displayed by a compound exhibiting matrix metalloprotease-inhibitory activity, which comprises subjecting to in situ zymography a specimen isolated from a mammal that has received the compound.

11. The method of claim 10, wherein the in situ zymography is conducted using a thin membrane which comprises gelatin or collagen together with a hardening agent, and which has a thickness of 1 $\mu$m to 20 $\mu$m.

12. The method of claim 10, wherein the in situ zymography is conducted by
   (1) contacting the isolated specimen onto the thin membrane comprising a substrate of matrix metalloprotease;
   (2) incubating the specimen-thin membrane sample;
   (3) staining and then decolorizing the thin membrane; and
   (4) verifying the tone developed on the thin membrane, and comparing the tone with that of the control.

13. The method of claim 12, wherein the substrate of the matrix metalloprotease is gelatin or collagen.

14. The method of claim 12, wherein the thin membrane comprises a hardening agent.

15. The method of claim 12, wherein the thin membrane has a thickness of 1 $\mu$m to 20 $\mu$m.

16. The method of claim 12, wherein the specimen is a tissue section having a thickness of 2 $\mu$m to 10 $\mu$m, and the incubation is conducted at 20° C. to 50° C. for 2 to 18 hours.

17. A method for determining quantitatively an in vivo matrix metalloprotease-inhibitory activity displayed by a compound exhibiting matrix metalloprotease-inhibitory activity, which comprises:
   (1) administering to a mammal a compound exhibiting matrix metalloprotease-inhibitory activity;
   (2) isolating a tissue or a fluid from the mammal to prepare a specimen;
   (3) contacting the isolated specimen onto a thin membrane comprising a substrate of matrix metalloprotease;
   (4) incubating the specimen-thin membrane sample;
   (5) staining and then decolorizing the thin membrane; and
   (6) verifying the tone developed on the thin membrane, and comparing the tone with that of the control.

18. The method of claim 17, wherein the specimen to be prepared has a thickness of 4 $\mu$m to 8 $\mu$m, and the incubation is conducted at 36° C. to 38° C. for 4 to 8 hours.

19. A method for determining quantitatively an anti-cancer activity of an anti-cancer agent exhibiting matrix metalloprotease-inhibitory activity, which comprises subjecting to in situ zymography a specimen isolated from a mammal that has received the anti-cancer agent, and evaluating for an in vivo matrix metalloprotease-inhibitory activity displayed by the agent as an indicator of the anti-cancer activity.

* * * * *

UNITED STATES PATENT AND TRADEMARK OFFICE
CERTIFICATE OF CORRECTION

PATENT NO.    : 6,627,411 B2
DATED         : September 30, 2003
INVENTOR(S)   : Ryuji Maekawa et al.

It is certified that error appears in the above-identified patent and that said Letters Patent is hereby corrected as shown below:

<u>Title page,</u>
Item [86], change the §371 (c)(1), (2), (4) date from "Nov. 23, 2001" to -- Feb. 28, 2002 --.

Signed and Sealed this

Tenth Day of February, 2004

JON W. DUDAS
*Acting Director of the United States Patent and Trademark Office*